United States Patent [19]

Davitashvili et al.

[11] Patent Number: 5,095,901

[45] Date of Patent: Mar. 17, 1992

[54] DEVICE FOR STIMULATION

[76] Inventors: Evgenia J. Davitashvili, ulitsa Vakhtangova, 3, kv.29; Alexandr M. Kleiman, Naberezhnaya Maxima Gorkogo, 40/42, kv.244, both of Moscow, U.S.S.R.

[21] Appl. No.: 515,593

[22] Filed: Apr. 19, 1990

[51] Int. Cl.$^5$ .............................................. A61N 5/06
[52] U.S. Cl. .................................................. 128/395
[58] Field of Search .............. 128/362, 381, 395, 396; 604/20

[56] References Cited

U.S. PATENT DOCUMENTS

| 3,648,706 | 3/1972 | Holzer | 128/395 |
| 4,492,221 | 1/1985 | Kerley | 128/362 |
| 4,556,064 | 12/1985 | Pomeranz et al. | 128/395 |

FOREIGN PATENT DOCUMENTS 388755 7/1973 U.S.S.R. .
1140797 2/1985 U.S.S.R. .
1258423 9/1986 U.S.S.R. .

OTHER PUBLICATIONS

D. Davitashvili, "Slushaju Svoi Ruki" (I Listen to my Hands), 1988, "Fizkultura i Sport" (Physical Training & Sport), p. 168.

*Primary Examiner*—William E. Kamm
*Attorney, Agent, or Firm*—Fleit, Jacobson, Cohn, Price, Holman & Stern

[57] ABSTRACT

A device for stimulating generally used in electro-magneto-radiotherapy for giving prophylaxis and psychological relief to patients. This device includes radiators on a movable support wherein the radiators are located within an outline of at least one hand on the support, a control unit connected to the radiators and a power supply connected to the control unit. The device makes it possible to create individual and multiuser psychological relief using conventional methods of non-contact messages to relieve fatigue, overstrain and stress.

3 Claims, 4 Drawing Sheets

DEVICE FOR STIMULATION

FIELD OF THE INVENTION

The present invention relates in general to electro-magneto-radiotherapy and more particularly to devices for stimulation.

The invention may be used for prophylaxis and psychological relief to patients and for exerting influence on various objects using physical fields having characteristics that correspond to those of physical fields of biological objects.

BACKGROUND OF THE INVENTION

A known method of exerting influence on biological objects is by radiating infrared radiation (8–14 μm), UHF-radiation (8–30 cm), and by using alternating electrical fields (10 Hz) (Davitashvili D., "Slushaju svoi ruki" (I listen to my hands), 1988, "Fizkultura i sport" (Physical Training and Sport"), Moscow, p. 168).

According to the above method the source of exerting influence are an operator's hands possessing the physical fields mentioned. The conventional method requires selecting operators and their individual teaching. Furthermore, this method lacks mechanization and automated dosing of physical influencing and, as such, requires inviting highly skilled specialists. A device is known for stimulation using infrared radiation (SU, A, 1258423); this device is able to produce necessary physical fields for every case and comprises: a radiating unit, a current amplifier, a pulse counter, and an indicator unit, connected in series; and also a generator connected to inputs of the pulse counter and current amplifier, a measuring/diagnostic unit, and biosensors. A required mode of infrared influence is chosen using the device units of imitation and pulse forming. To estimate infrared influence efficiency the device further comprises the biosensors connected to the measuring/diagnostic unit having a biorhythm characteristic selector equipped with an indicator and a mode indexer through a controlled commutator. However, the conventional device does not make it possible to adjust the radiators characteristics along the electrodes surfaces and, consequently, to imitate non-contact stimulation using the operator's hands.

Still another device is known for stimulation using UHF fields (SU, A, 388755) comprising a self-excited oscillator, a power supply unit, a control unit, a dipole radiator with a screen, and a power meter. When the self-excited oscillator lamp anode is energized the oscillator forms UHF oscillations which go to the power meter through a capacitor coupler and then to the radiator input along a HF-cable. The device provides constant dosing during any procedure and at any orientation of body parts to be radiated in respect to the radiators. However, during medicinal influence there is no possibility to adjust the radiators characteristics along the surface (inside the outline) of the electrodes and, consequently, to imitate non-contact types of stimulation using the operator's hands.

Still another device is known for stimulation by acting on an operator with electrical fields (SU, A, 1140797); this device comprises radiators mounted on a movable support, a power supply unit, and connected in series a generator, an attenuator, mode of action indicators, and a control unit, the latter being connected to the radiators.

The dosing accuracy stems from automatic counting of reflected, from a bioobject, pulses and maintaining a proportional relationship between the electrode/bioobject distance and radiation level. The required range of radiation levels on the electrodes is maintained by the generator through the control unit, commutator, and attenuator. However, the above device does not make operative (corrective) adjusting of radiation intensity possible.

SUMMARY OF THE INVENTION

It is an object of the present invention to expand functional characteristics of the stimulating device.

The nature of the invention is for stimulation and comprises a movable support, radiators for exerting physical fields on the object to be radiated and mounted on said support, at least one hand outline pictured on said movable support, said radiators being located within said at least one hand outline and forming a radiating surface, a control unit for setting the needed parameters of the radiators physical fields and constructed as a regulator of radiation intensity from different areas of the radiating surface, said regulator being connected to said radiators, and a power supply unit for energizing said control unit and said radiators and connected to said control unit and electrically bound with said radiators.

It is advisable to use, as a radiation intensity regulator, a stabilized power supply for the radiators and connected to it a distributor and a commutator with the radiators connected to the latter, the commutator control input being connected to the distributor.

It is possible for the radiation intensity regulator to comprise groups of an emitter follower, a variable resistor, and a multiposition switch, connected in series, the latter being connected to the radiators.

By virtue of automatic radiation dosing the present invention makes the effectiveness of exerting a physical fields influence higher. Because of locating the radiators on the support inside the hand print boundaries and constructing the control unit as a radiation intensity regulator and using as radiators their combination from the group: an alternating electrical field source, an infrared radiation source, an UHF source of radiation and heat, the present invention makes non-contact influence of the above fields quite adequate. The same can be said about designing the movable support as a two part structure, each part having radiators within the boundaries of the left and right hands respectively. The present invention makes it possible to create both individual and multiuser means of psychological relief and to use conventional methods of non-contact massage for relief of large groups of people having hard and tiring work (assembly line workers, drivers, aeroport operators, etc.) of fatigue, overstrain, and stresses.

BRIEF DESCRIPTION OF THE DRAWINGS

Other objects and advantages of the present invention will become apparent upon reading the following description of the preferred embodiment and upon reference to the drawings.

DETAILED DESCRIPTION OF THE INVENTION

Figure 1:
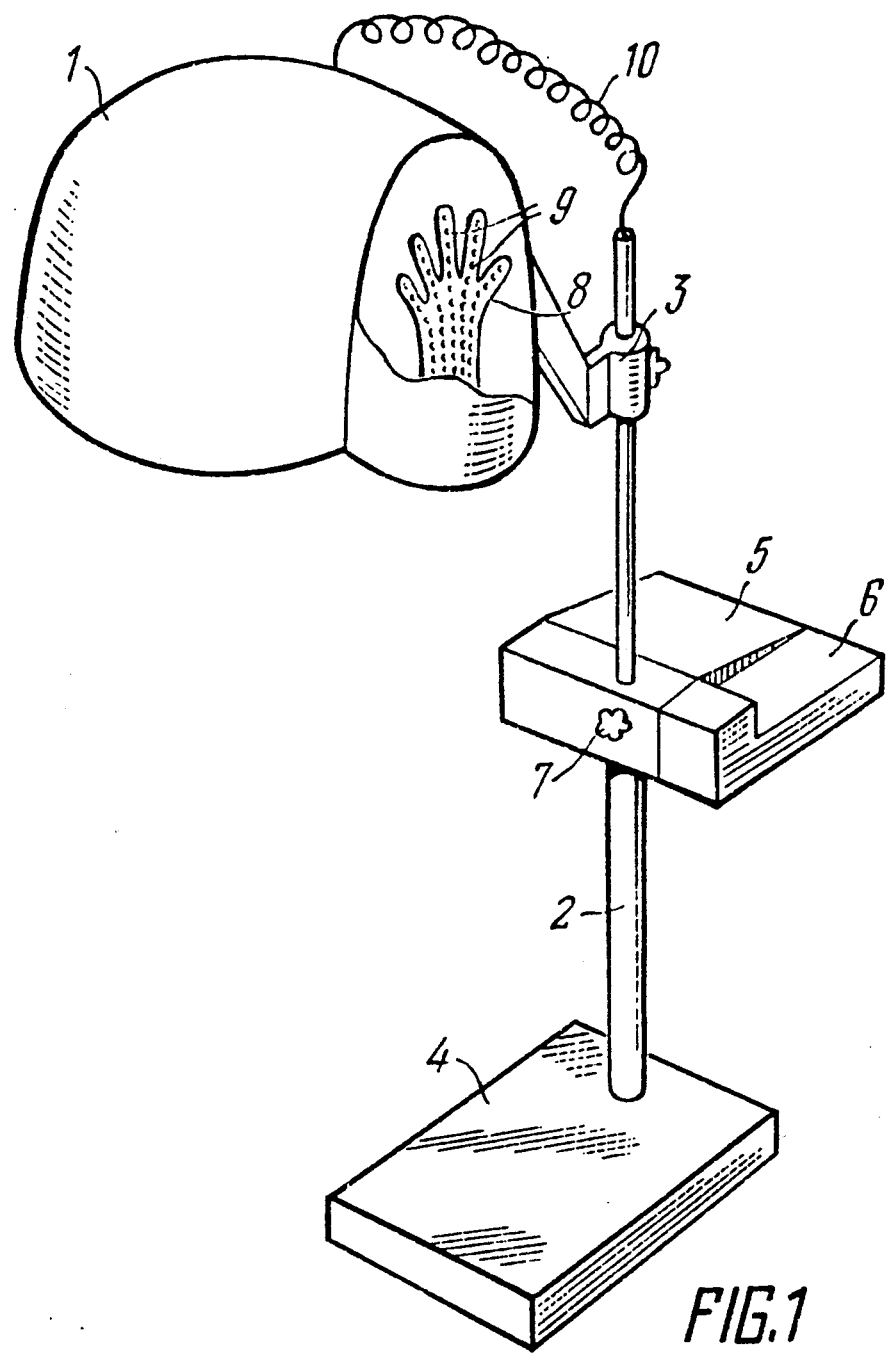
FIG. 1 is a design solution for the stimulating device shown isometrically and in accordance with the present invention.

The stimulating device comprises a movable support 1 (FIG. 1) mounted (using fixing element 3) on a rod 2 and fixed in a base 4. The stimulating device further comprises a control unit 5 and power supply unit 6 both located inside the case fixed to the rod 2 using a fixing element 7. On the movable support 1 there is pictured at least one hand outline 8 on which radiators 9 forming a radiating surface are positioned. Radiators 9 are connected in parallel groups $9_1$ (FIG. 2), $9_2$, $9_3$, ..., $9_n$.

Control unit 5 (FIG. 1) and power supply unit 6 are connected to radiators 9 using flexible cord 10.

Figure 2:
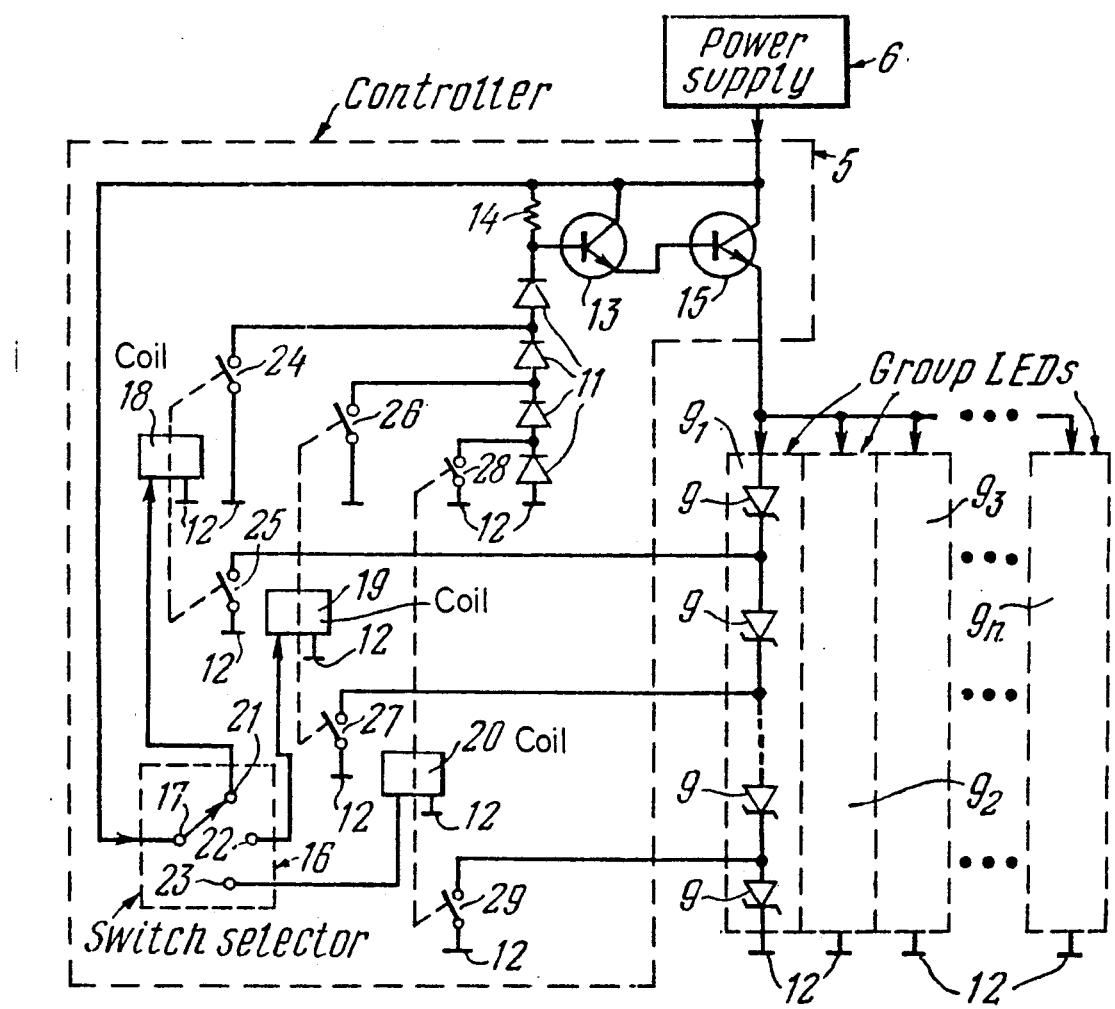
FIG. 2 is a block-diagram of the stimulating device having a radiation intensity regulator with a stabilized power supply unit in accordance with the present invention.

Control unit 5 is intended for setting the necessary parameters of physical fields of the radiators and designed as a radiation intensity regulator for various areas of the radiating surface and is connected to the radiators 9. The radiation intensity regulator comprises a stabilized power supply unit having Zener diodes 11 connected in series (FIG. 2). One of the anodes is connected to a bus 12 of zero potential. Then there is transistor 13 having its base connected (through resistor 14) to power supply unit 6 and the cathode of one of Zener diodes 11, and a transistor 15 having its base connected to the emitter of transistor 13, the collectors of both transistors 13 and 15 being connected to each other and to power supply unit 6, and the emitter of transistor 15 being connected to radiators 9. In each group $9_1$, $9_2$, $9_3$, ..., $9_n$ radiators 9 are connected in series, the anode of radiator 9 at each group input being connected to the emitter of transistor 15 and the cathode of radiator 9 at each group output being connected to bus 12 of zero potential. The radiation intensity regulator comprises distributor 16 in the form of a three-position switch wiper 17 which is connected to power supply unit 6.

The radiation intensity regulator further comprises a commutator having relays; coils 18, 19 and 20 of these relays are connected to contacts 21, 22 and 23 of distributor 16 respectively and to bus 12 of zero potential on their other sides. Contact group 24 of relay coil 18 is connected to the anode of Zener diode 11 the cathode of which is connected to the base of transistor 13. Contact group 24 is connected to bus 12 of zero potential on the other side. Contact group 25 of relay coil 18 is connected to the cathode of a radiators, the anode of which radiator is connected to the emitter of transistor 15. Contact group 25 is connected to bus 12 of zero potential on the other side. Contact group 26 of relay coil 19 is connected to the anode of a Zener diode 11 the cathode of which is connected to contact group 24. Contact group 26 is connected to bus 12 of zero potential on the other side. Contact group 27 of relay coil 19 is connected to the cathode of a radiator 9 the anodes of which are connected to contact group 25. Contact group 27 is connected to bus 12 of zero potential on the other side. Contact group 28 of relay coil 20 is connected to a anode of the Zener diode 11 the cathode of which is connected to contact group 26. Contact group 28 is connected to bus 12 of zero potential on the other side. Contact group 29 of relay coil 20 is connected to the cathode of a radiator 9 the anodes of which radiator are connected to contact group 27. Contact group 29 is connected to bus 12 of zero potential on the other side.

Radiators 9 are intended to exert physical fields on the object to be radiated. In the described embodiment of the present invention semiconductor diodes are used for radiators 9, the former produce radiation influence on the object in heat, visible light, infrared, and UHF bands.

If in different groups semiconductor radiators of different bands are used it becomes possible to exert complex influence (comprising UHF, IR, light, and heat types of radiation) on the object.

Figure 3:
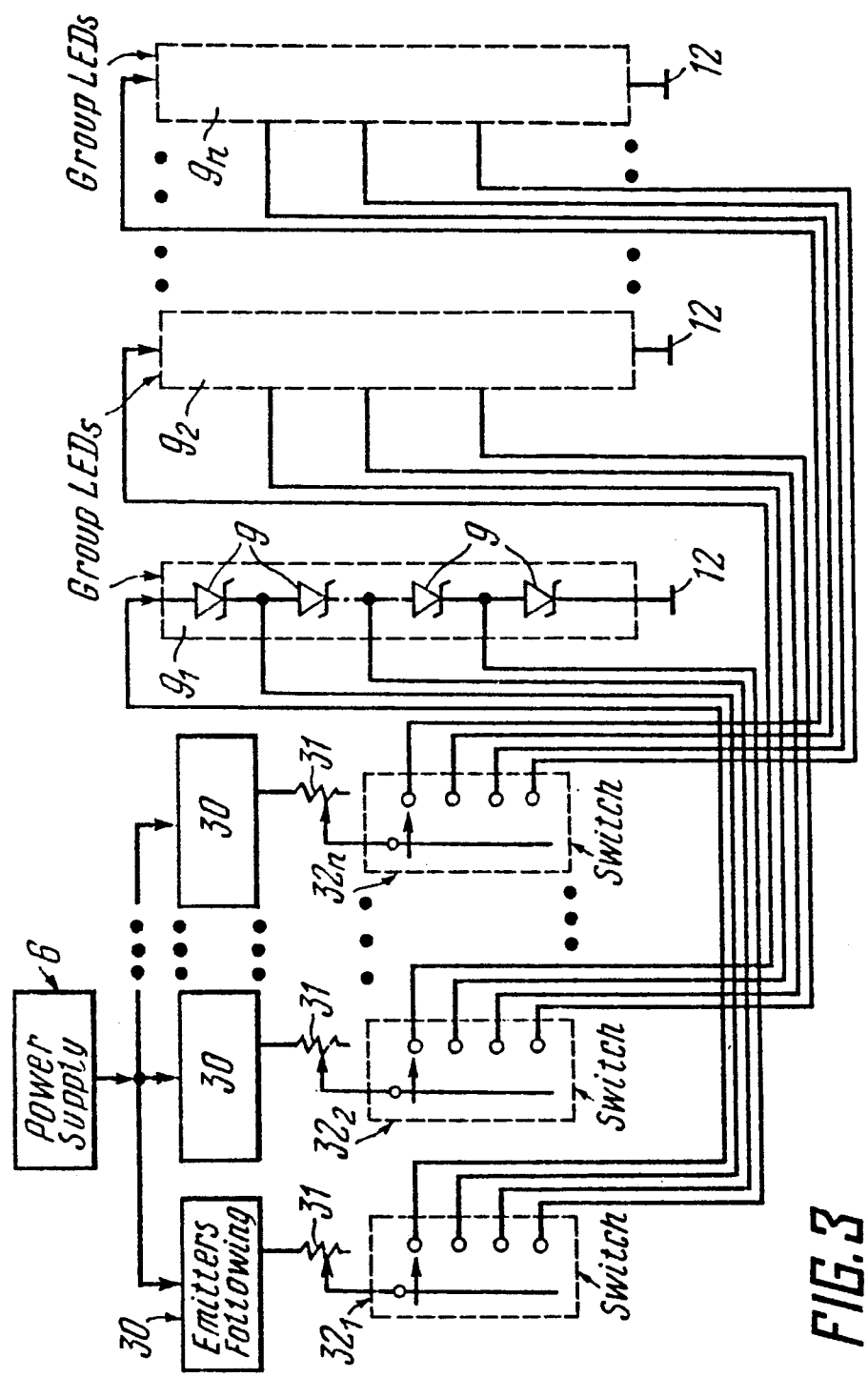
FIG. 3 is a functional diagram of the stimulating device having a radiation intensity regulator with variable resistors and multiposition switches in accordance with the present invention.

In another embodiment the radiation intensity regulator comprises n groups of radiators connected in series, emitter follower 30 (FIG. 3), variable resistor 31, and multiposition switch 32. Multiposition switch 32 of the first group is connected to radiators 9 of group $9_1$, and switch 32 of the n-th group is connected to radiators 9 of group $9_n$.

Figure 4:
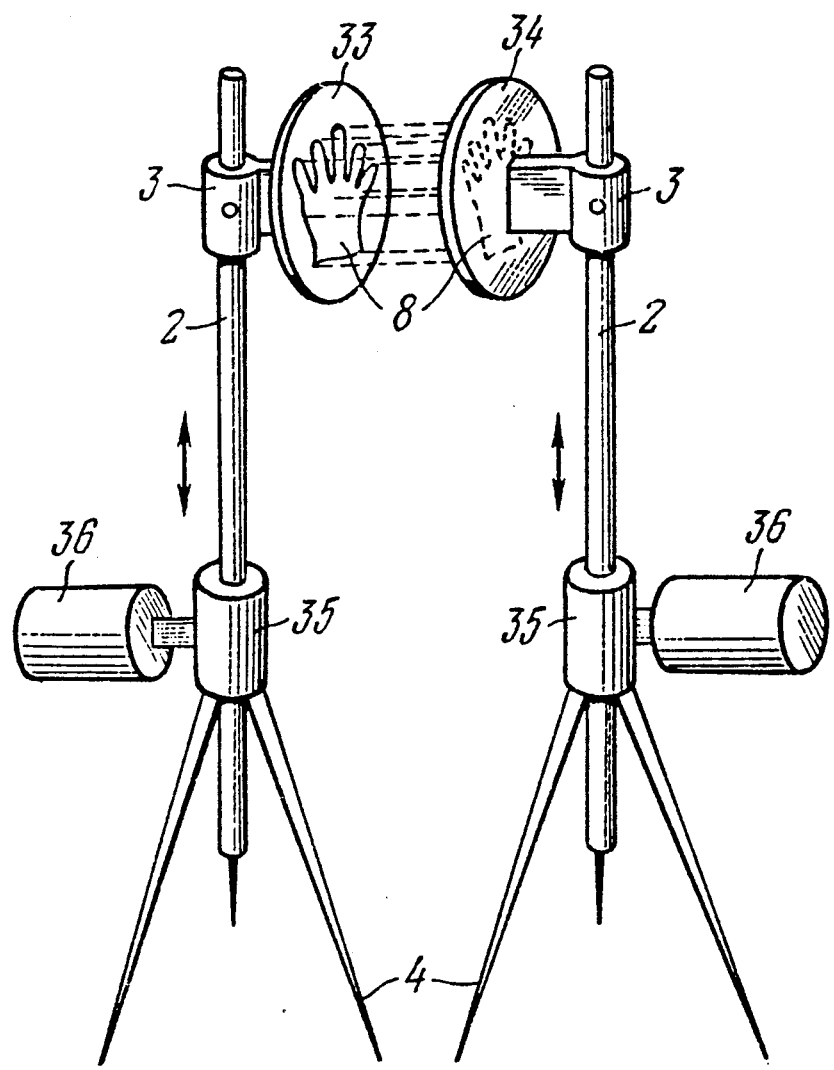
FIG. 4 illustrates a design solution for the mechanical part of the stimulating device with a two part movable support, the radiators of each part being located within the boundaries of the left and right hand prints, respectively, in accordance with the present invention.

Movable support 1 may consist of two parts 33 and 34 (FIG. 4), each of them being mounted on rod 2 using fixing element 3. On base 4, in the form of a tripod, sleeve 35 is mounted; rod 2 can move vertically through this sleeve because of step motor 36. Such a design makes it possible to imitate movements of two operator's hands in the vertical plane.

The stimulating device operates as follows:

Power supply unit 6 (FIG. 1) is switched on, being energized from the mains (not shown). Using radiation intensity regulator of control unit 5 the needed radiation intensity is set for radiators 9. On different areas of surface 8 the level of radiation may be different; e.g. radiation intensity is higher in the centre of the hand than in the other areas of surface 8. The necessary radiation level and distribution pattern of radiation intensity over surface 8 for the object to be radiated are set in accordance with the procedure prescribed. When working such a procedure out the physician takes into account the field intensity diagrams of the operator specially trained in methods of non-contact massage. The object is located in the vicinity of surface 8 and radiated during the prescribed time. The necessary radiation levels for radiators 9 are set as follows:

When distributor 16 (FIG. 2) is in one of its positions (e.g. contacts 17 and 22 are closed) coil 19 of the commutator becomes energized. Contact group 26 of the corresponding relay connects two Zener doides 11 to bus 12 of zero potential; thus on the base of transistor 13 and on the emitter of transistor 15 there exists a voltage level corresponding to the reference voltage on two remaining connected in series Zener diodes 11. From the emitter of transistor 15 the voltage is applied to groups $9_1$, $9_2$, $9_3$, ... $9_n$ of radiators 9. Contact group 27 of relay coil 19 of the commutator also connects some of radiators 9 in groups $9_1$, $9_2$, $9_3$, ..., $9_n$ to bus 12 of zero potential.

The stabilized power supply unit maintains constant current flow through remaining radiators 9, the radiation intensity of each of remaining radiators 9 being maximum.

In the other positions of distributor 16 the number of radiators 9 not connected to bus 12 of zero potential in groups $9_1$, $9_2$, $9_3$, ..., $9_n$ changes in proportion to the number of Zener diodes not connected to the same bus. Thus distributor 16 stepwise changes radiation intensity of that part of surface 8 that has groups $9_1, 9_2, 9_3, \ldots, 9_n$ mounted on it. Distributor 16 may be in the form of an electronic commutator controlled by a computer in which case the procedure prescribed and stored as a program takes place operatively with automatic maintaining of the necessary radiation intensity.

Groups $9_1, 9_2, 9_3, \ldots, 9_n$ of radiators 9 can be located on surface 8 with maximum density.

Thus it is possible to vary radiation intensity over the area of surface 8, e.g. increasing it in the centre of the hand and progressively decreasing it towards the finger tips. The voltage from power supply unit 6 (FIG. 3) is applied to radiators 9 through emitter followers 30, variable resistors 31, and multiposition switches 32, whereby smooth adjustment of radiation levels from surface 8 (FIG. 1) is accomplished.

When using radiators 9 of different types, e.g. radiators of visible and infrared bands, variable resistors 31 are used to set modes for the radiators of each type.

If in accordance with the procedure prescribed it becomes necessary to change surface 8 (FIG. 4) positions along the objects, rods 2 move vertically with the help of step motors 36, two parts 33 and 34 of the movable support being also moved in the vertical plane to radiate the object from both sides.

Thus the stimulating device of the present invention makes it possible to exert on the object influence of different physical fields (their superposition included). In other words we have medicinal actions which (by virtue of automated dosing of radiation intensity from surface 8 repeating the form and radiation characteristics of the trained operator's hands) do not differ from actual non-contact massage.

Time of stimulation is not limited that is why the device can operate for long periods and may be advantageous in aviation and cosmonautics applications.

What is claimed is:

1. A device for stimulation comprising:
   a movable support,
   radiators for exerting physical fields on the object to be radiated and mounted on said movable support,
   at least one hand outline pictured on said movable support, wherein
   said radiators being located within said at least one hand outline and forming a radiating surface,
   a control unit for setting parameters of physical fields of the radiators and designed as a radiation intensity regulator from different areas of the radiating surface, said regulator being connected to said radiators, and
   a power supply unit for energizing said control unit and radiators and is connected to said control unit and electrically bound with said radiators.

2. A device for stimulation according to claim 1 further comprising a stabilized power supply unit included in said radiation intensity regulator for the radiators and have a distributor and a commutator connected to it, the radiators being connected to the commutator and having a commutator control input connected to the distributor.

3. A device for stimulation according to claim 1 wherein the radiation intensity regulator comprises groups of an emitter follower, a variable resistor, and a multiposition switch connected in series, the latter being connected to the radiators.

* * * * *